United States Patent
Beckers et al.

(10) Patent No.: US 11,207,051 B2
(45) Date of Patent: Dec. 28, 2021

(54) WEARABLE ULTRASOUND PATCH AND APPLICATION METHOD OF SUCH A PATCH

(71) Applicant: KONINKLIJKE PHILIPS N.V., Eindhoven (NL)

(72) Inventors: Lucas Johannes Anna Maria Beckers, Veldhoven (NL); Franciscus Johannes Gerardus Hakkens, Eersel (NL); Edward Theodorus Maria Berben, Herten (NL); Timon Rutger Grob, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 21 days.

(21) Appl. No.: 16/649,259

(22) PCT Filed: Sep. 13, 2018

(86) PCT No.: PCT/EP2018/074829
§ 371 (c)(1),
(2) Date: Mar. 20, 2020

(87) PCT Pub. No.: WO2019/057616
PCT Pub. Date: Mar. 28, 2019

(65) Prior Publication Data
US 2020/0289087 A1    Sep. 17, 2020

(30) Foreign Application Priority Data
Sep. 20, 2017 (EP) .................... 17192009

(51) Int. Cl.
*A61B 8/00* (2006.01)

(52) U.S. Cl.
CPC .......... *A61B 8/4236* (2013.01); *A61B 8/4281* (2013.01)

(58) Field of Classification Search
CPC ........ A61B 8/08; A61B 8/4236; A61B 8/4281
See application file for complete search history.

(56) References Cited

U.S. PATENT DOCUMENTS

| 4,820,753 A | 4/1989 | Caprette, Jr. et al. |
| 5,265,614 A | 11/1993 | Hayakawa et al. |
| 2005/0074407 A1 | 4/2005 | Smith |

(Continued)

FOREIGN PATENT DOCUMENTS

| DE | 3133434 A | * | 3/1983 |
| DE | 3133434 A1 | | 3/1983 |
| WO | 2011163570 A2 | | 12/2011 |

OTHER PUBLICATIONS

International Search Report and Written Opinion for International Application No. PCT/EP2018/074829, filed Sep. 13, 2018, 13 pages.

*Primary Examiner* — Boniface N Nganga (57) ABSTRACT

A wearable patch (10) comprising an ultrasound transducer (30) mounted on the patch, the ultrasound transducer comprising a major surface for contacting the skin of a wearer of the patch, said major surface being covered by a layer (33) of a soluble adhesive precursor, the wearable patch further comprising a seal ring (40) extending from the patch, said seal ring surrounding the ultrasound transducer. Also disclosed are a wearable patch kit, assembly and application method.

12 Claims, 6 Drawing Sheets

(56) References Cited

U.S. PATENT DOCUMENTS

| | | | |
|---|---|---|---|
| 2005/0148996 A1* | 7/2005 | Sun | A61Q 19/10 604/501 |
| 2006/0015058 A1 | 1/2006 | Kellogg et al. | |
| 2006/0253078 A1* | 11/2006 | Wu | A61M 37/0015 604/173 |
| 2007/0087060 A1 | 4/2007 | Dietrich et al. | |
| 2007/0208280 A1 | 9/2007 | Talish et al. | |
| 2008/0200810 A1* | 8/2008 | Buchalter | A61B 8/4236 600/459 |
| 2012/0065479 A1* | 3/2012 | Lahiji | A61B 5/02411 600/301 |
| 2012/0277640 A1 | 11/2012 | Lewis, Jr. et al. | |
| 2014/0276048 A1* | 9/2014 | Kiley | A61B 8/4236 600/438 |

* cited by examiner

WEARABLE ULTRASOUND PATCH AND APPLICATION METHOD OF SUCH A PATCH

RELATED APPLICATIONS

This application is the U.S. National Phase application under 35 U.S.C. § 371 of International Application No. PCT/EP2018/074829, filed on Sep. 13, 2018, which claims priority to and the benefit of European Application No. 17192009.3, filed Sep. 20, 2017. These applications are hereby incorporated by reference herein.

FIELD OF THE INVENTION

The present invention relates to a wearable patch comprising an ultrasound transducer mounted on the patch.

The present invention further relates to a wearable patch assembly including such a wearable patch.

The present invention further relates to a wearable patch kit including such a wearable patch.

The present invention further relates to a method of applying such a wearable patch to a patient's skin region.

BACKGROUND OF THE INVENTION

Ultrasound data acquisition such as ultrasound imaging is an increasingly important diagnostic tool. In addition to high resolution imaging in hospitals and other medical practices, ultrasound imaging is more increasingly being used for patient monitoring over a prolonged period of time. In such a scenario, the patient typically wears a patch including an ultrasound transducer comprising one or more ultrasound transducer cells, which transducer is used to monitor a particular part of the patient's anatomy over such a time period.

The use of such wearable ultrasound patches for instance is contemplated for haemodynamic monitoring, in which parameters such as blood flow, pulse pressure, pulse wave velocity, cardiac output and cross-sectional dimensions of arteries may be monitored, bladder monitoring, e.g. within the clinical settings of a hospital, in which patient urine production and hydration rates may be monitored, coronary chronic total inclusion (CTO) monitoring to visualize large CTOs (>10 cm) that cannot be visualized using contrast-enhanced fluoroscopy and vascular access monitoring for the purpose of ultrasound-based diagnosis and treatment of peripheral diseases. Other applications of such longer-term ultrasound patient monitoring will be apparent to the skilled person.

As is well-known per se, in order to achieve a good acoustic coupling between the ultrasound transducer and the patient's body, a coupling agent, i.e. fluid, such as an ultrasound conductive gel typically is applied between the ultrasound transducer and the patient's body. During application of such an ultrasound transducer to the patient's body, pressure is applied to evacuate air bubbles from the coupling agent in order to establish the desired acoustic contact. The duration of ultrasound investigations in a clinical setting such as a hospital is relatively short, e.g. 5-15 minutes, which means that the coupling agent does not have time to dry out or otherwise degrade.

Such a coupling agent is equally desirable when applying a wearable ultrasound patch to a patient's body in order to establish the desired acoustic coupling between the patch and the patient's body. However, the use of a coupling agent in this context is not without challenges. Firstly, care has to be taken that the coupling agent does not interfere with the adhesion of the patch to the patient's body in case of an adhesive patch. Moreover, degradation of the coupling agent over the period during which the patch is worn by the patient must be prevented as much as possible.

It is known to apply an adhesive gel between the patient-facing surface of the ultrasound transducer of such a wearable patch and the skin region of a patient that can act as a coupling agent. For example, US 2005/0074407 A1 discloses a biocompatible and bio-excretable lubricant and coupling fluid or gel comprising polyvinylpyrrolidone (PVP) and/or polyvinyl alcohol (PVA) dissolved in water. However, these gels are reported in this prior art application to be insufficient to adhere an ultrasound probe to a patient's skin region as the sole medium of adhesion.

A further challenge when applying such coupling agents is that air evacuation from the coupling agent should be easily achievable. The latter is not straightforward as limited amounts of the coupling agent should be used to avoid interference with adhesive layers of the patch (if present), but this brings about the risk of insufficient coupling agent remaining in between the patch and the patient's body when pressure is applied to the patch to evacuate such air bubbles.

SUMMARY OF THE INVENTION

The present invention seeks to provide a wearable patch comprising an ultrasound transducer mounted on the patch that can be effectively coupled to the skin of a patient in a straightforward manner.

The present invention further seeks to provide a wearable patch assembly including such a wearable patch.

The present invention further seeks to provide a wearable patch kit including such a wearable patch.

The present invention further seeks to provide a method of applying such a wearable patch to a patient's skin region.

According to an aspect, there is provided a wearable patch comprising an ultrasound transducer mounted on the patch, the ultrasound transducer comprising a major surface for contacting the skin of a wearer of the patch, said major surface being covered by a layer of a soluble adhesive precursor, the wearable patch further comprising a seal ring extending from the patch, said seal ring surrounding the ultrasound transducer. The present invention is based on the realization that an adhesive contact fluid may be formed in situ on the skin of a patient by the provision of a precursor of such an adhesive contact fluid on the surface of the ultrasound transducer such that upon application of an appropriate solvent to the layer of the soluble adhesive precursor, the adhesive contact fluid is formed in between the ultrasound transducer and the region of the skin of the patient to which the wearable patch is applied. The seal ring may be used to prevent the formed adhesive coupling layer between the ultrasound transducer and the skin of the patient to which the wearable patch is applied from drying out, thereby prolonging the lifetime of this coupling layer and the operational time of the wearable patch as a consequence.

In the context of the present application, a layer of a soluble adhesive precursor is a layer of a solid material, typically a polymer material, which is a dry layer, i.e. a layer substantially free of moisture or solvent. The provision of such a layer of a soluble adhesive precursor material on the ultrasound transducer facilitates excellent control over the amount of adhesive contact fluid to be formed in between the ultrasound transducer and the region of the skin of the patient to which the wearable patch is applied and furthermore ensures that the formation of air bubbles in the adhesive contact fluid is largely avoided, thereby improving the acoustic coupling between the ultrasound transducer and the skin region of the patient to which the wearable patch is to be applied.

The soluble adhesive precursor preferably is an adhesive gel precursor in order to form an interface between the ultrasound transducer and the skin region of the patient to which the wearable patch is applied that has excellent acoustic coupling properties.

The soluble adhesive precursor preferably is water-soluble, that is, water preferably is applied to the soluble adhesive precursor layer in order to form the adhesive acoustic coupling between the ultrasound transducer and the skin region of the patient to which the wearable patch is applied, although it should be understood that other solvents, e.g. biocompatible solvents, may be used as well.

Any suitable soluble adhesive precursor material may be applied to the major surface of the ultrasound transducer, such as PVP or PVA. PVA is particularly preferred because of the contact gel that results from the dissolving of PVA in water as an acoustic impedance similar to that of the patient's skin, thereby providing a coupling fluid that facilitates high-quality ultrasound imaging of the part of the patient's anatomy of interest. At this point, it is further noted that a surprising insight of the present invention is that due to the relatively small form factor of the ultrasound transducer on the wearable patch according to embodiments of the present invention, adhesive gels formed from polymers such as PVA or PVP are sufficiently adhesive to retain the wearable patch against the skin of the patient over a prolonged period of time, i.e. several hours, which typically is long enough to facilitate the ultrasound imaging of the patient's anatomy of interest, contrary to the teachings in US 2005/0074407 A1, where it was stipulated that for ultrasound probes (which typically have a larger form factor than the ultrasound transducers of the wearable patch is according to embodiments of the present invention) such adhesive coupling gels were insufficiently adhesive to form the sole means of adhesion of such a probe against the skin of a patient.

The wearable patch may further comprise a first conduit extending through the patch for applying a solvent to the layer of the soluble adhesive precursor such that the solvent, e.g. water, may be applied to the soluble adhesive precursor layer on the ultrasound transducer surface after the wearable patch has been positioned on a skin region of the patient, thereby preventing the need to wet the patient's skin prior to application of the wearable patch. In this embodiment, the wearable patch preferably further comprises a second conduit extending through the patch for venting air from an interface between the layer of the soluble adhesive precursor and the skin of the wearer of the patch upon application of the patch to the skin such that any air bubbles between the ultrasound transducer and the skin region of the patient can be displaced and vented from the interface between the ultrasound transducer and the skin region of the patient through the second conduit in response to the solvent being administered to the first conduit.

The second conduit of the wearable patch may further comprise an air-permeable and water-impermeable layer to prevent water from escaping from in between the wearable patch and the patient's skin in case the solvent is water, e.g. to prevent drying out of the adhesive coupling layer as previously explained. For example, the air-permeable and water-impermeable layer may be a hydrophobic membrane that repels water but allows air to pass through the membrane such that air can be expelled from the interface between the ultrasound transducer and the skin region of the patient whilst preventing loss of water from this interface.

The wearable patch may further comprise a breakable reservoir comprising a solvent for dissolving the soluble adhesive precursor, wherein the breakable reservoir is positioned such that upon breaking the container the solvent contacts the layer of the soluble adhesive precursor. This has the advantage that a metered portion of the solvent can be supplied integral to the wearable patch, thereby reducing the risk that the applicant of the wearable patch applies an incorrect amount of the solvent. Furthermore, the presence of such a reservoir avoids the need to insert the solvent through the first conduit after application of the wearable patch against a skin region of the patient, thereby providing a particularly user-friendly wearable patch.

According to another aspect, there is provided a wearable patch assembly comprising the wearable patch according to any of the herein described embodiments and a control module attachable to the ultrasound transducer through a cable or wire, said control module comprising circuitry for controlling the operation of the ultrasound transducer and for processing the ultrasound images captured with the ultrasound transducer.

According to yet another aspect, there is provided a wearable patch kit comprising the wearable patch according to any of the herein described embodiments and a container containing the solvent for dissolving the layer of the soluble adhesive precursor. Such a kit has the advantage that the wearable patch may be supplied without also having to supply a coupling fluid such as a coupling gel, which makes it more straightforward for an end-user such as a medical professional or even a patient to apply the wearable patch to a region of the skin of the patient. In a preferred embodiment, the solvent is water although other biocompatible solvents may also be used.

According to still another aspect, there is provided a method of applying the wearable patch of any of the herein described embodiments to a skin region of a patient, the method comprising positioning the wearable patch onto the skin region; and forming an adhesive layer between the ultrasound transducer and the skin region by dissolving the layer of the soluble adhesive precursor in a solvent. This has the advantage that an adhesive coupling agent does not have to be separately applied between the wearable patch and the skin region of the patient, thereby providing greater control over the amount of such a coupling agent that is applied and facilitating the removal of air bubbles from the in situ formed adhesive coupling agent.

In a first embodiment, forming an adhesive layer between the ultrasound transducer and the skin region comprises wetting the skin region with the solvent prior to positioning the wearable patch onto the skin region, which has the advantage that the solvent, e.g. water, may be applied in a straightforward manner.

In an alternative embodiment, forming an adhesive layer between the ultrasound transducer and the skin region comprises injecting the solvent through the patch after positioning the wearable patch onto the skin region. This has the advantage that the amount of water to be added can be accurately controlled and that the wearable patch can be positioned in different locations prior to activating the adhesive coupling layer, thereby giving greater flexibility in the application of the wearable patch to the skin of the patient. Moreover, in this embodiment the solvent can be applied to non-horizontal surfaces, thereby preventing run-off of the solvent, e.g. water, when applied prior to application of the wearable patch to the skin region of the patient.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
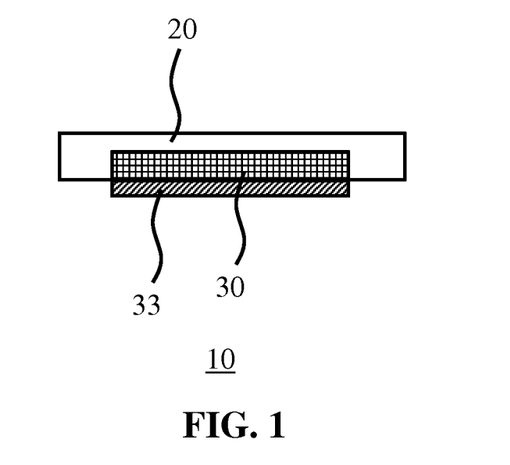
FIG. 1 schematically depicts a cross-sectional view of a wearable patch according to an embodiment.

FIG. 1 schematically depicts a cross-sectional view of a wearable patch 10 according to an embodiment of the present invention. The wearable patch 10 comprises a housing 20 into which an ultrasound transducer 30 is housed. The housing may be any suitable container, such as a container made of a polymer or metal (aluminium for instance) or combinations thereof. Inside the housing 20 a carrier such as a PCB on which an ultrasound transducer may be mounted, optionally together with some other electronic components as will be explained in further detail below. The ultrasound transducer 30 may comprise one or more ultrasound transducer cells arranged in a one-dimensional or two-dimensional array of transducer cells or elements, such as a 4×4 mm array having 16 ultrasound transducer elements with a pitch in a range of 200-300 microns, by way of non-limiting example. Other dimensions are of course equally feasible. The ultrasound transducer 30 typically is operable in a transmit mode in which the ultrasound beams are generated and a receive mode in which the ultrasound transducer 30 is operable to receive echo signals induced by the generated ultrasound beams within the body of the individual wearing the wearable patch 10.

In an embodiment, the ultrasound transducer elements are operable in a frequency range of 2-12 MHz, although other frequency ranges may be contemplated. Any suitable type of ultrasound transducer elements may be used for this purpose, e.g. piezoelectric transducer (PZT) elements, capacitive micro-machined ultrasound transducer (CMUT) elements, piezoelectric micro-machined transducer (PMUT) elements, and so on, although CMUT elements are particularly preferred, in particular over (PZT) elements due to their superior (adjustable) resonance frequency range, which make CMUT elements particularly suitable for patient monitoring purposes. As such transducer elements are well-known per se, they will not be explained in further detail for the sake of brevity only. The array of transducer cells may be arranged as a phased array to facilitate beam steering of an ultrasound beam generated with the ultrasound transducer 30. Again, such beam steering is well-known per se and will not be explained in further detail for the sake of brevity only.

A major surface of the ultrasound transducer 30 arranged to contact a skin region of a patient upon application of the wearable patch 10 to this skin region carries a layer 33 of a soluble precursor material of an adhesive coupling layer such as an adhesive coupling gel such that upon contact of the layer 33 with the appropriate solvent, e.g. water in case of a water-soluble precursor material, the layer 33 dissolves in the solvent and forms the adhesive coupling layer between the ultrasound transducer 30 and the skin region of the patient onto which the wearable patch 10 is applied. Materials that may be used for the water-soluble precursor material include polymers such as PVA and PVP although any material that upon contact with a solvent such as water forms a gel, e.g. a hydrogel that can be used as an adhesive coupling layer between the major surface of the ultrasound transducer 30 and the skin region of a patient may be used for this purpose. It is noted that PVA is specifically mentioned because a coupling gel formed from PVA has an acoustic impedance that closely matches the acoustic impedance of skin, therefore making it particularly suitable for use in the layer 33.

The layer 33 may have a thickness in the range of 5-500 μm, preferably of 10-100 μm, which ensures that a sufficiently thick layer of the adhesive coupling gel may be formed from which air bubbles may be easily evacuated. This is an important insight of embodiments of the present invention, as the provision of a dry layer 33 of the soluble adhesive precursor to a controlled thickness on the major surface of the ultrasound transducer 30 for contacting the skin region of the patient provide accurate control of the amount of adhesive coupling agent to be formed by dissolving the layer 33 in the appropriate solvent as previously explained. An acoustic window material (not shown) may be present over the patient-facing major surface of the ultrasound transducer 30 to provide acoustic impedance matching of the ultrasound transducer cells of the ultrasound transducer 30 to the skin of the patient. The acoustic window material if present is typically positioned in between the major surface of the ultrasound transducer 30 and the dry layer 33 of the soluble adhesive precursor, i.e. the layer 33 may be applied over the acoustic window material. Non-limiting examples of such an acoustic window material include a (particle-filled) silicone layer and a layer stack including a soft polybutadiene rubber layer with a TPX (polymethylpentene) top layer to protect the ultrasound transducer 30 as well as the patient from the driving voltage of the ultrasound transducer 30, such that this TPX layer is sandwiched in between the soft polybutadiene rubber layer and the dry layer 33.

Figure 2:
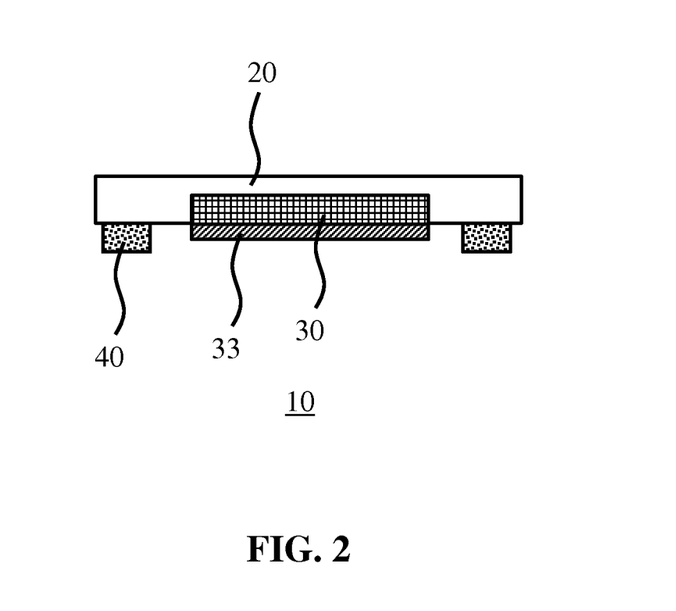
FIG. 2 schematically depicts a cross-sectional view of a wearable patch according to another embodiment.
Figure 3:
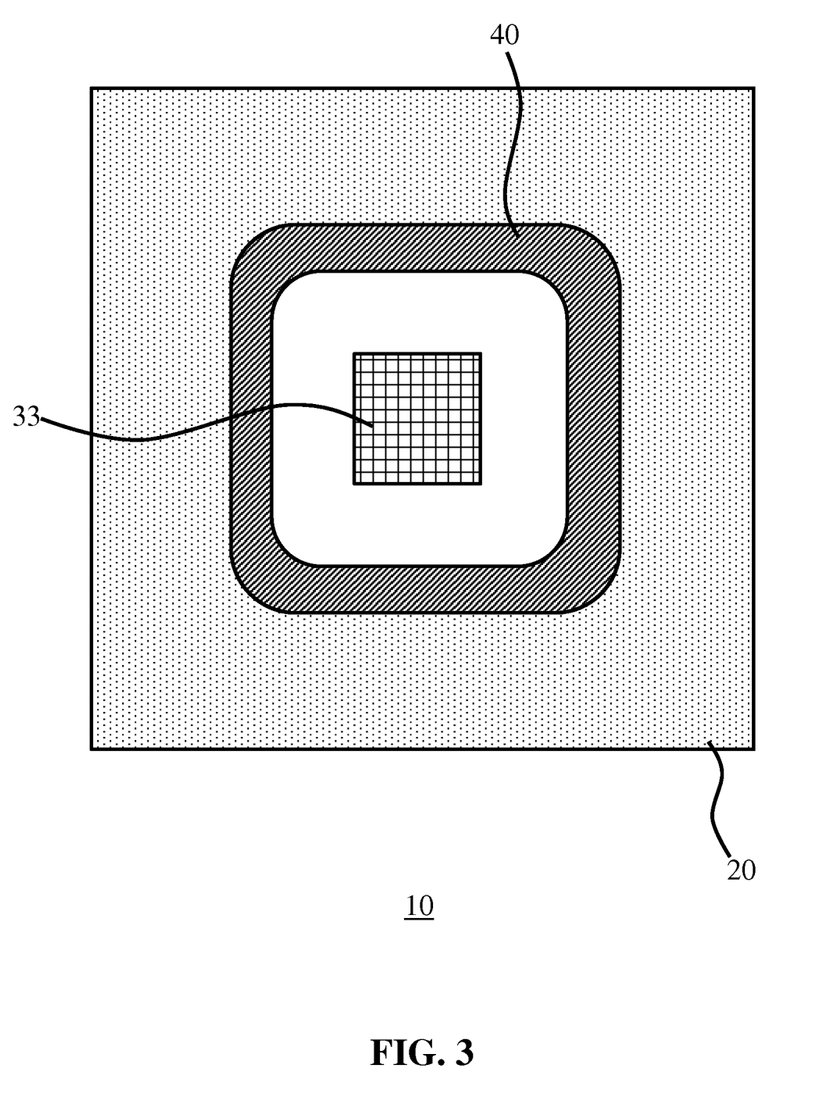
FIG. 3 schematically depicts a face-on view of a wearable patch as shown in FIG. 2.

FIG. 2 schematically depicts a cross-sectional view and FIG. 3 schematically depicts a face-on view of a wearable patch 10 according to another embodiment. In this embodiment, the wearable patch 10 further comprises a seal ring 40 surrounding the ultrasound transducer 30 such that upon application of the wearable patch 10 on the skin region of the patient the seal ring 40 closes off the ultrasound transducer 30 from its surroundings, thereby preventing or at least substantially reducing the evaporation of the solvent from the adhesive coupling agent formed from dissolving the layer 33 of the soluble adhesive precursor in this solvent, thereby preventing the adhesive coupling medium from drying out too quickly. The seal ring 40 is shown to have a rectangular closed outline by way of non-limiting example only as it should be understood that the seal ring may have any suitable closed shape, e.g. a circular shape.

The seal ring 40 may be made of any suitable material, e.g. a flexible material such as a rubber or another elastomer or from a rigid material. The seal ring 40 in some embodiments may be porous such that air evacuated from the interface in between the ultrasound transducer 30 and the skin region of the patient can escape from underneath the wearable patch 10 through the pores of the seal ring 40.

Figure 4:
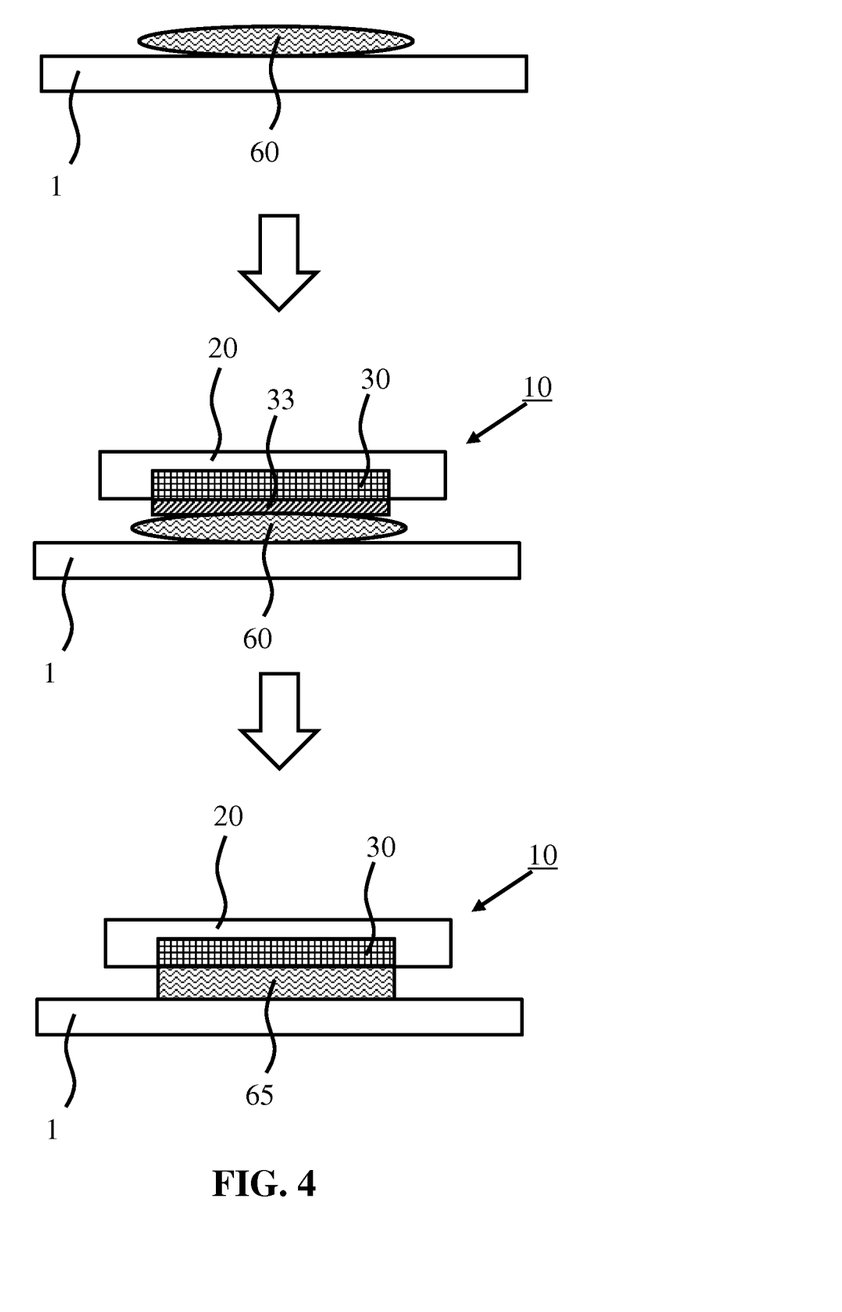
FIG. 4 schematically depicts an application method of a wearable patch to a skin region of a patient according to an embodiment.

In the aforementioned embodiments, the solvent for dissolving the layer 33 of the soluble adhesive precursor in order to form the adhesive layer, e.g. an adhesive coupling gel, between the ultrasound transducer 30 and the skin region of the patient typically is applied to the skin region of the patient prior to positioning of the wearable patch 10 thereon. Such an application method is schematically depicted in FIG. 4, in which a volume of the solvent 60, e.g. water or another biocompatible solvent, is applied to the skin region 1 of the patient. The volume of the solvent 60 may be a metered volume to ensure that a suitable amount of the solvent 60 is applied to the skin region 1, i.e. an amount that is sufficient to form the adhesive layer without diluting this layer too much.

Next, the wearable path 10 is positioned on the wetted portion of the skin region 1, i.e. the skin region 1 carrying the volume of the solvent 60, such that the surface of the ultrasound transducer 30 carrying the layer 33 of the soluble adhesive precursor is brought into contact with the volume of the solvent 60. This causes the soluble adhesive precursor to be dissolved in the volume of the solvent 60, thereby forming the adhesive layer 65, preferably an adhesive coupling gel, which adheres the wearable patch 10, or more accurately, the major surface of the ultrasound transducer 30, to the skin region 1 of the patient. Due to the way this adhesive layer 65 is formed, the presence of air bubbles in this layer is largely avoided, thus providing a coupling layer between the ultrasound transducer 30 and the skin region 1 of the patient having particularly good acoustic properties.

In an example experiment, a layer 33 of PVA was applied to the patient-facing major surface of an ultrasound transducer 30 incorporated in a wearable patch 10, and applied to a skin region 1 wetted with water. It was found that the resulting PVA gel had excellent adhesive properties as demonstrated by the wearable patch 10 still being satisfactorily adhered to the skin region 1 after 3 hours, with the PVA gel being substantially free of air bubbles.

Figure 5:
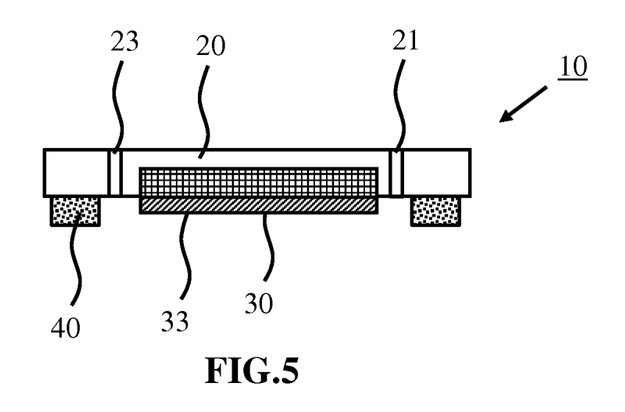
FIG. 5 schematically depicts a cross-sectional view of a wearable patch according to yet another embodiment.

FIG. 5 schematically depicts a cross-sectional view of an alternative embodiment of the wearable patch 10, in which the wearable patch 10 further comprises a first conduit 21 extending through the patch through which the solvent can be injected such that the wearable patch 10 can be positioned onto a dry region 1 of the patient's skin without the need to first apply the solvent 60 to the skin region 1. This for example is advantageous in scenarios where the wearable patch 10 is to be applied to a skin region 1 in a non-horizontal orientation, where the application of the solvent 60 to the skin region 1 would cause run-off of the solvent, thereby hampering the formation of the adhesive layer 65 in the desired location on the patient's skin. In this embodiment, the seal ring 40 preferably is present to contain the solvent 60 to be injected within the volume delimited by the wearable path 10 and the seal ring 40 when positioned on the skin region 1 of the patient.

In FIG. 5, the first conduit 21 is formed through the housing 20 of the wearable patch 10 by the way of non-limiting example only. It is for instance equally feasible that the first conduit 21 extends through the seal ring 40 such that the solvent 60 may be brought into contact with the layer 33 of the adhesive precursor material on the major surface of the ultrasound transducer 30 by injecting the solvent 60 through the seal ring 40.

In an embodiment, the wearable patch 10 further comprises a second conduit 23 acting as an air vent through which air trapped in between the wearable patch 10 and the skin region 1 of the patient when the wearable patch 10 is pressed against the skin region 1 can be evacuated when the solvent 60 is injected through the first conduit 21. As before, the second conduit 23 may be present in the wearable patch 10 in any suitable location, e.g. extending through the housing 20 as shown in FIG. 5 or extending through the seal ring 40 instead. Alternatively, the second conduit 23 may be omitted if the seal ring 40 is porous, such that the aforementioned trapped air can be evacuated from in between the wearable patch 10 and the skin region 1 through the pores of the seal ring 40.

Figure 6:
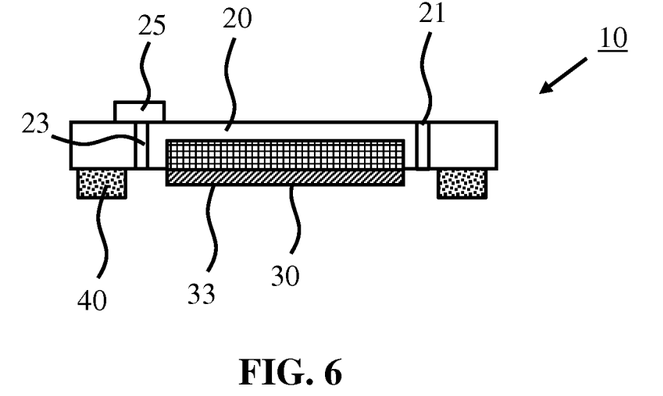
FIG. 6 schematically depicts a cross-sectional view of a wearable patch according to yet another embodiment.

The first conduit 21 and the second conduit 23 if present may be sealed off after insertion of the solvent 60, e.g. by a plug, cork or the like in order to prevent the solvent 60 from evaporating through these conduits once the wearable patch 10 is adhered to the skin region 1. Alternatively, as schematically depicted in FIG. 6, the second conduit 23 may comprise an air-permeable and water-impermeable sealing layer 25 such as a hydrophobic membrane, a Gore-Tex layer or any other water-repellent breathable material such that air can be evacuated from in between the wearable patch 10 and the skin region 1 of the patient whilst water is prevented from escaping from the second conduit 23 by the air-permeable and water-impermeable sealing layer 25 such that drying out of the adhesive layer 65 is suppressed by the presence of the air-permeable and water-impermeable sealing layer 25 in the second conduit 23 without having to manually seal the second conduit 23 after application of the solvent 60 through the first conduit 21.

Figure 7:
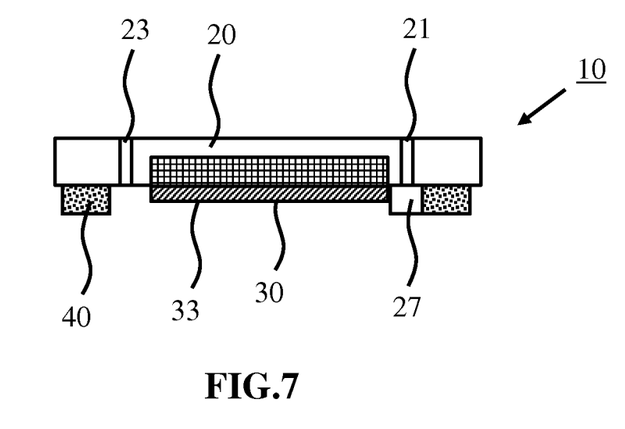
FIG. 7 schematically depicts a cross-sectional view of a wearable patch according to yet another embodiment.

FIG. 7 schematically depicts yet another embodiment of the wearable patch 10, in which the wearable patch 10 further comprises a breakable reservoir 27 filled with the solvent 60 such that upon breaking the reservoir 27, e.g. by piercing the reservoir 27, the solvent 60 is released from the reservoir 27 and contacts the layer 33 of the adhesive precursor material on the major surface of the ultrasound transducer 30, thereby forming the adhesive layer 65 as previously explained. For example, the reservoir 27 may be a plastic pouch or the like aligned with the first conduit 21 such that a needle of the like may be inserted through the first conduit 21 in order to break the reservoir 27 and release the solvent 60 into the cavity in between the wearable patch 10 and the skin region 1 of the patient such that the solvent 60 can dissolve the layer 33 on the patient-facing surface of the ultrasound transducer 30 in order to form the adhesive layer 65 between the ultrasound transducer 30 and the skin region 1. In this embodiment, the seal ring 40 preferably is present to prevent spillage of the solvent 60 from underneath the wearable patch 10. The second conduit 23 may be present to facilitate the evacuation of air as previously explained although in this embodiment the volume of the solvent 60 for dissolving the layer 33 is already present within the space or cavity in between the wearable patch 10 and the skin region 1 of the patient such that the air does not necessarily need to be evacuated from this space or cavity.

Figure 8:
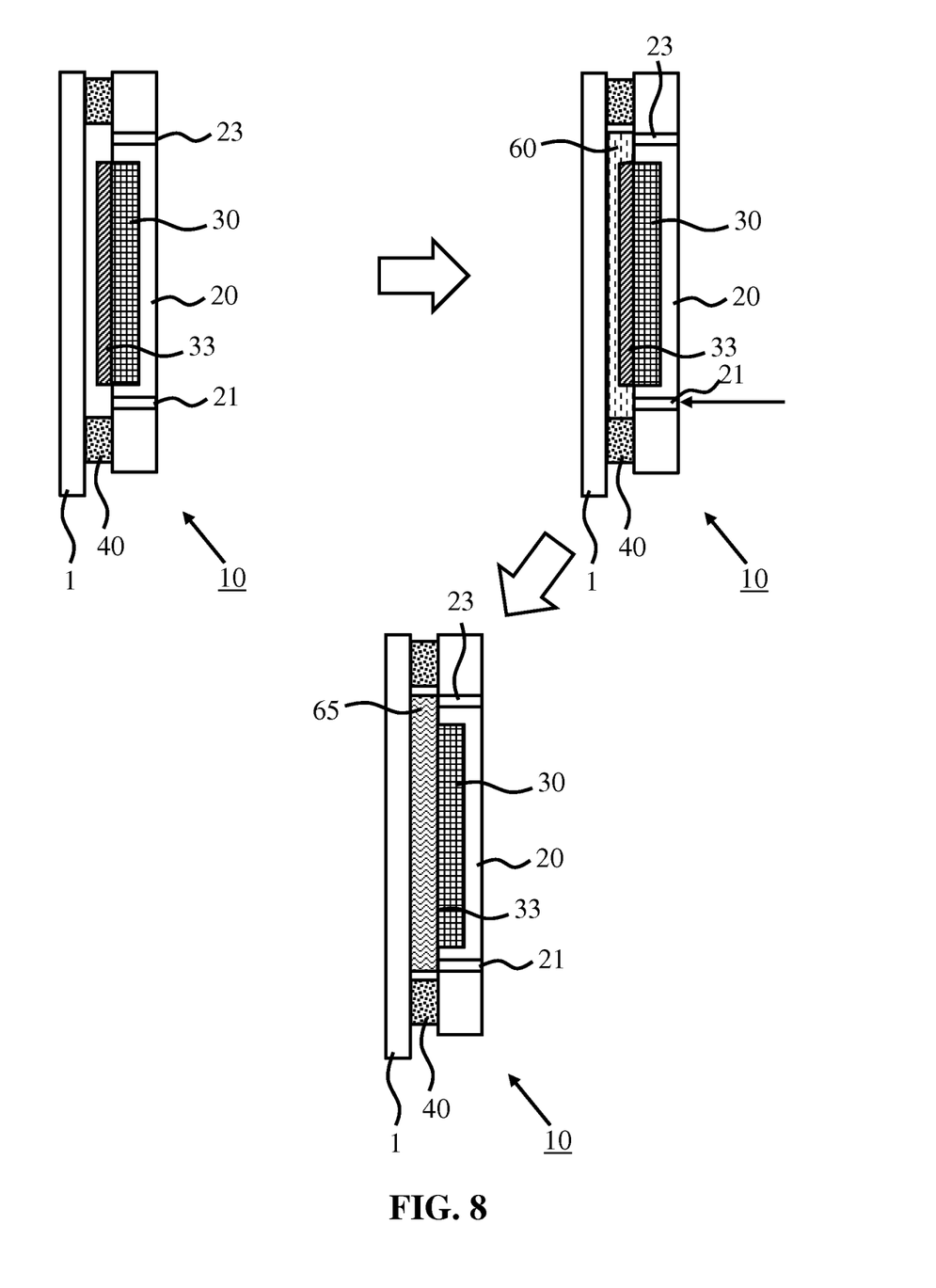
FIG. 8 schematically depicts an application method of a wearable patch to a skin region of a patient according to another embodiment.

FIG. 8 schematically depicts an application method of the wearable patch 10 to a skin region 1 of the patient according to another embodiment. In this embodiment, the wearable patch 10 is first positioned on a dry region 1 of the skin of the patient, i.e. a skin region 1 to which no solvent 60 is applied, after which the solvent 60 is injected into the space or cavity in between the wearable patch 10 and the skin region 1 through the first conduit 21 in the wearable patch 10, as indicated by the black arrow. The solvent 60, e.g. water, may first dissolve the periphery of the layer 33 of the adhesive precursor material after which the solvent 60 may diffuse through the dissolved portion of the layer 33 to dissolve the more central regions of the layer 33 in order to form the adhesive layer 65 that adheres the ultrasound transducer 30 to the skin region 1 of the patient. Alternatively, a clearance may exist between the layer 33 of the adhesive precursor material and the skin region 1 of the patient, which clearance may be penetrated by the solvent 60 such that a larger initial surface area of the layer 33 is dissolved by the solvent 60 such that the adhesive layer 65 may be formed more rapidly. As previously explained, air displaced by the injection of the solvent 60 into the space or cavity in between the wearable patch 10 and the skin region 1 of the patient may be evacuated from this space or cavity through the seal ring 40 and/or through the second conduit 23. This application method is particularly suited to apply the wearable patch 10 to a non-horizontal skin region 1, as run-off of the solvent 60 is prevented by the seal ring 40 when the solvent 60 is applied through the first conduit 21.

The wearable patch 10 according to embodiments of the present invention may be provided together with a container comprising a solvent, e.g. a bottle of water or the like to form a wearable patch kit 10 according to embodiments of the present invention. The amount of solvent 60 in the container may be metered such that the correct amount of solvent 60 is applied to the wearable patch 10 when adhering the wearable patch 10 to the skin region 1 of the patient as previously explained.

Figure 9:
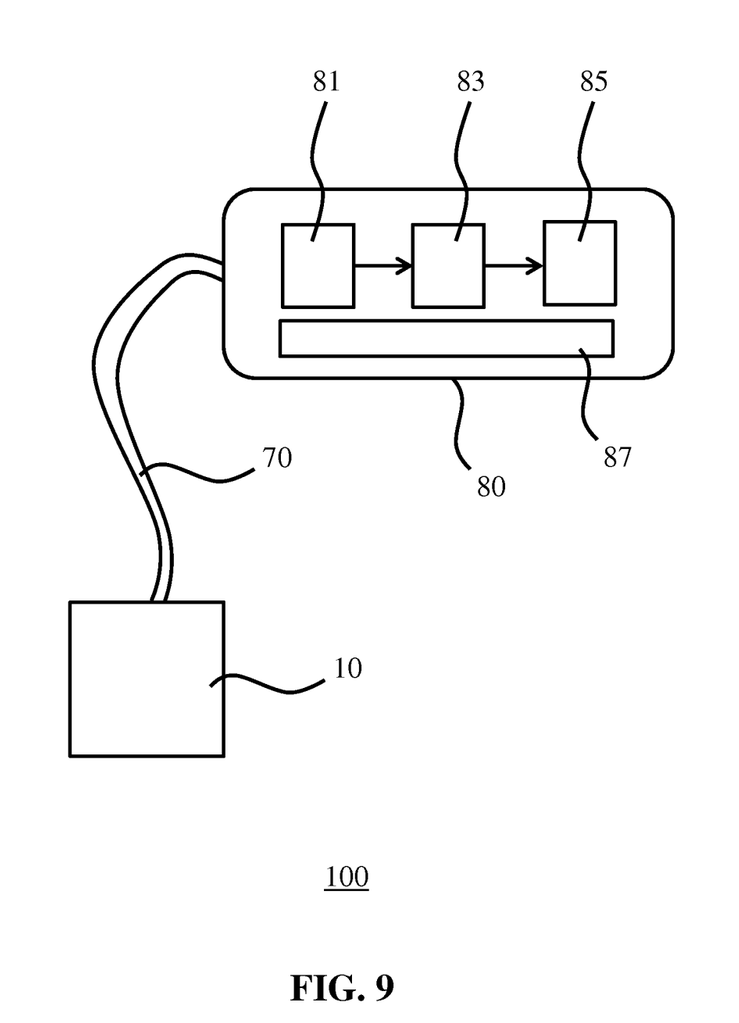
FIG. 9 schematically depicts a wearable patch assembly according to an embodiment.

FIG. 9 schematically depicts a wearable patch assembly 100 comprising the wearable patch 10 according to embodiments of the present invention and a control module 80 for controlling the ultrasound transducer 30. The control module 80 may be connected to the ultrasound transducer 30 through a wire or cable 70, which may be any suitable wire or cable, e.g. a coaxial cable, a cable comprising individually insulated wires, a ribbon comprising conductive tracks, and so on. The control module 80 may comprise circuitry 81 for controlling the ultrasound transducer 30. For example, the circuitry 81 may include an array controller coupled to a down conversion stage, which may form part of the array controller or may be a separate entity. The down conversion stage may apply noise filtering and frequency down conversion of the echo signals, e.g. from the MHz domain to the KHz domain, and employ a signal envelope to the down converted echo signals to reduce the amount of data that needs to be provided to a signal processor for deriving the desired bladder information from the acquired echo signals. Other suitable data reduction techniques will be immediately apparent to the skilled person.

The circuitry 81 may further comprise a signal processor for processing the signals received from the ultrasound transducer 30. Alternatively, such a signal processor may form part of a remote device, e.g. a wearable smart device such as a smart watch, a portable smart device such as a mobile phone or tablet computer, a laptop computer, a personal computer, or the like in order to reduce the computational effort required from the wearable patch 10 such that the lifetime of the battery 87 within the control module 80 may be extended.

The circuitry 81 may be communicatively coupled to a data storage device 83, e.g. a memory or the like, on-board the control module 80, with a wireless communication module 85 communicatively coupled to the data storage device 83 such that the data pertaining to the acquired echo signals as stored in the data storage device 83 may be periodically communicated to a remote device, e.g. in response to a communication request from the remote device. Any suitable wireless communication protocol, e.g. Bluetooth, Wi-Fi, a mobile communication protocol such as 3G, 4G, 5G or the like, a near field communication protocol (NFC), and so on, may be deployed for the communication between the control module 80 and the remote device.

As mentioned previously, the data pertaining to the acquired echo signals communicated from the control module 80 to such a remote device preferably is reduced in size to minimize the amount of data that needs to be communicated in this manner in order to extend the lifetime of the battery 87. It should be understood that in alternative embodiments in which the circuitry 81 comprises the signal processor, the wireless communication module 85 may be used to communicate a processing result of the signal processor to such a remote device, e.g. for visualization of the processing result on a display of the remote device.

In yet a further embodiment, the control module 80 is configured to upload the data pertaining to the acquired echo signals with a wireless communication module 85 into a remote data repository acting as an intermediary data storage device from which the remote device may download the stored data. This has the advantage that the remote device does not have to be within communication range of the wireless communication module 85 but instead may download the data at any suitable point in time to evaluate this data. For example, the remote data repository may be a cloud storage solution or the like, which may be accessed by both the wireless communication module 85 and the remote device over a network connection such as the Internet, in which case the wireless communication module 85 may establish a wireless connection with an Internet hub such as a router or the like within communication range of the wireless communication module 85 through which the data pertaining to the acquired echo signals may be uploaded into the remote data repository.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A wearable patch comprising an ultrasound transducer mounted on the patch, the ultrasound transducer comprising a major surface for contacting the skin of a wearer of the patch, said major surface being covered by a layer of a soluble adhesive precursor, the wearable patch further comprising a seal ring extending from the patch, said seal ring surrounding the ultrasound transducer; and a breakable reservoir comprising a solvent for dissolving the soluble adhesive precursor, wherein the breakable reservoir is positioned such that upon breaking the container the solvent contacts the layer of the soluble adhesive precursor.

2. The wearable patch of claim 1, wherein the soluble adhesive precursor is an adhesive gel precursor.

3. The wearable patch) of claim 1, wherein the soluble adhesive precursor is water-soluble.

4. The wearable patch of claim 1, wherein the soluble adhesive precursor is polyvinyl alcohol.

5. The wearable patch of claim 1, further comprising a first conduit extending through the patch for applying a solvent to the layer of the soluble adhesive precursor.

6. The wearable patch of claim 5, further comprising a second conduit extending through the patch for venting air from an interface between the layer of the soluble adhesive precursor and the skin of the wearer of the patch upon application of the patch to the skin.

7. The wearable patch of claim 6, wherein the second conduit comprises an air-permeable and water-impermeable layer.

8. A wearable patch assembly comprising the wearable patch according to claim 1 and a control module attachable to the ultrasound transducer through a cable or wire, said control module comprising circuitry for controlling the operation of the ultrasound transducer and for processing the ultrasound images captured with the ultrasound transducer.

9. The wearable patch kit of claim 1, wherein the solvent is water.

10. A method of applying the wearable patch of claim 1 to a skin region of a patient, the method comprising:

positioning the wearable patch onto the skin region; and forming an adhesive layer between the ultrasound transducer and the skin region by dissolving the layer of the soluble adhesive precursor in the solvent.

11. The method of claim 10, wherein forming an adhesive layer between the ultrasound transducer and the skin region comprises wetting the skin region with the solvent prior to positioning the wearable patch onto the skin region.

12. The method of claim 10, wherein forming an adhesive layer between the ultrasound transducer and the skin region comprises injecting the solvent through the wearable patch after positioning the patch onto the skin region.

* * * * *